(12) United States Patent
Mannen

(10) Patent No.: US 8,039,434 B2
(45) Date of Patent: Oct. 18, 2011

(54) METHOD FOR PRODUCING HUMAN INSULIN-LIKE GROWTH FACTOR I

(75) Inventor: Teruhisa Mannen, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 533 days.

(21) Appl. No.: 12/112,450

(22) Filed: Apr. 30, 2008

(65) Prior Publication Data

US 2009/0053767 A1 Feb. 26, 2009

Related U.S. Application Data

(60) Provisional application No. 60/914,907, filed on Apr. 30, 2007.

(51) Int. Cl.
*A61K 38/30* (2006.01)
*A61K 39/05* (2006.01)
*C07K 14/65* (2006.01)
*C12N 1/02* (2006.01)

(52) U.S. Cl. .. 514/8.5; 530/303; 424/245.1; 435/252.33

(58) Field of Classification Search .................. None
See application file for complete search history.

(56) References Cited

U.S. PATENT DOCUMENTS

| | | | |
|---|---|---|---|
| 5,231,178 A | 7/1993 | Holtz et al. | |
| 5,324,639 A | 6/1994 | Brierley et al. | |
| 6,080,844 A * | 6/2000 | Carney et al. | 530/361 |
| 6,331,414 B1 | 12/2001 | Lee et al. | |
| 7,071,313 B1 | 7/2006 | Cowgill et al. | |

FOREIGN PATENT DOCUMENTS

| | | |
|---|---|---|
| JP | 2002-291476 | 10/2002 |
| WO | WO 93/19084 | 9/1993 |

OTHER PUBLICATIONS

Nilsson et al.—Expression and Purification of Recombinant Insulin-like Growth Factors from *Escherichia coli*. Methods in Enzymology vol. 198, 3-16, Peptide Growth Factors Part C 1991.*

Rinderknech, E., et al., "The Amino Acid Sequence of Human Insulin-Like Growth Factor I and Its Structural Homology with Proinsulin," The Journal of Biological Chemistry, vol. 253, No. 8, Issue of Apr. 25, 1978, pp. 2769-2776.

Iwai, M, et al., "Direct Identification of Disulfide Bond Linkages in Human Insulin-Like Growth Facto I (IGF-I) by Chemical Synthesis," J. Biochem., vol. 106, No. 6, 1989, pp. 949-951.

Humbel, R. E., et al., "Insuling-Like Growth Factors I and II," Eur. J. Biochem., vol. 190, 1990, pp. 445-462.

Savage, M. O., et al., "Therapeutic Application of the Insulin-Like Growth Factors," Growth Hormone & IFG Research, 14, 2004, pp. 301-308.

Gasparini, L., et al., "Potential Roles of Insulin and IFG-1 in Alzheimer's Disease," Trends in Neurosciences, vol. 26, No. 8, Aug. 2003, pp. 404-406.

Ren, J., et al., "Insulin-Like Growth Factor I as a Cardiac Hormone: Physiological and Pathophysiological Implications in Heart Disease," J. Mo. Cell Cardiol, vol. 31, 1999, pp. 2049-2061.

Sato, A., et al., "Three-Dimensional Solution Structure of a Disulfide Bond Isomer of the Human Insulin-Like Growth Factor-I," J. Peptide Res., vol. 56, 2000, pp. 218-230.

M. Date, et al., "Secretion of human epidermal growth factor by *Corynebacterium glutamicum*", Letters in Applied Microbiology, vol. 42, No. 1, XP009102872, ISSN: 0266-8254, Jan. 2006, pp. 66-70.

Sun-Ok Kim, et al., "High-level expression and simple purification of recombinant human insulin-like growth factor I", Journal of Biotechnology, Elsevier Science Publishers, vol. 48, No. 1, XP004037039, ISSN: 0168-1656, Jul. 18, 1996, pp. 97-105.

Roger A. Hart, et al., Effect of environment on insulin-like growth factor I refolding selectivity[1], Biotechnology and Applied Biochemistry, Academic Press, vol. 20, No. Part 2, XP000579045, ISSN: 0885-4513, Oct. 1, 1994, pp. 217-232.

* cited by examiner

*Primary Examiner* — Elly-Gerald Stoica

(74) *Attorney, Agent, or Firm* — Oblon, Spivak, McClelland, Maier & Neustadt, L.L.P.

(57) ABSTRACT

A method is provided for producing hIGF-I with high purity and yield. This is a method for producing human insulin-like growth factor I, having a step of removing modified human insulin-like growth factor I from the human insulin-like growth factor I, the step including:

(A) a step of adjusting the pH of a culture liquid of a human insulin-like growth factor I producing bacteria to 8 or more after completion of culture;
(B) a step of letting the culture liquid obtained in step (A) stand; and
(C) a step of removing the producing bacteria from the culture liquid obtained in step (B).

13 Claims, 1 Drawing Sheet

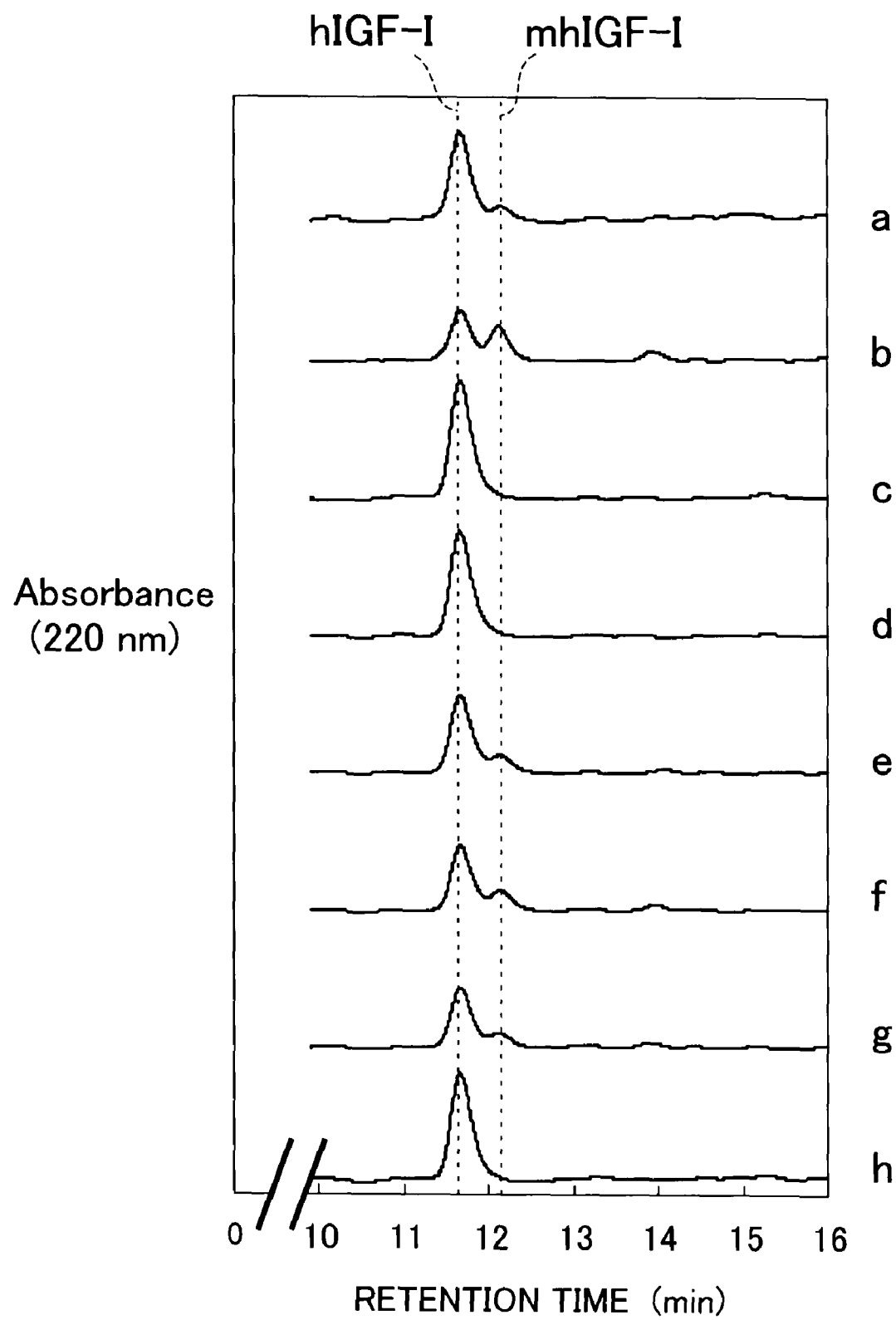

SEQUENCE LISTING

```
<160> NUMBER OF SEQ ID NOS: 10

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 1
ggccctgaaa ctctgtgtgg tgccgaactg gtggatgcct tgcagtttgt              50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgttaaaat agaagccgcg atcgccgcac acaaactgca aggcatccac              50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcggcttct attttaacaa accaaccggt tacggttcca gctcccgccg              50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cactcatcga cgattccggt tgtggagcg cggcgggagc tggaaccgta               50

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accggaatcg tcgatgagtg ctgtttccgc agctgcgacc tccgccgcct              50

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctctagat catgcggatt ttgcgggctt caggggtgcg cagtacatct ccaggcggcg   60
gaggtcgcag ct                                                      72

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
ggccctgaaa ctctgtgtgg                                                  20

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcctctagat catgcggatt ttgcgggct                                        29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggtaccc aaattcctgt gaattagctg                                       30

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccacacagag tttcagggcc tgccgttgcc acaggtgcgg                             40
```

METHOD FOR PRODUCING HUMAN INSULIN-LIKE GROWTH FACTOR I

CROSS-REFERENCE TO RELATED APPLICATIONS

The present application claims priority to U.S. provisional patent application 60/914,907, filed on Apr. 30, 2007.

BACKGROUND OF THE INVENTION

1. Field of the Invention

The present invention relates to a method for producing human insulin-like growth factor I (hereinafter abbreviated as hIGF-I). Specifically, it relates to a method for producing hIGF-I whereby hIGF-I can be obtained with high purity and yield by letting a culture liquid of a hIGF-I producing bacteria stand under specific conditions.

2. Description of the Related Art hIGF-I is a known polypeptide compound existing in nature (E. Rinderknecht et al., "The amino acid sequence of human insulin-like growth factor I and its structural homology with proinsulin", J. Biol. Chem., 1978, 253(8): p. 2769-76; M. Iwai et al., "Direct identification of disulfide bond linkages in human insulin-like growth factor I (IGF-I) by chemical synthesis", J. Biochem. (Tokyo), 1989, 106(6): p. 949-51) and having cell proliferation activity (R. E. Humbel, "Insulin-like growth factors I and II", Eur. J. Biochem., 1990, 190(3): p. 445-62).

hIGF-I can itself be used as a drug, and drug applications are being developed (see for example M. O. Savage et al., "Therapeutic applications of the insulin-like growth factors", Growth Horm. IGF Res., 2004, 14(4): p. 301-8; L. Gasparini et al., "Potential roles of insulin and IGF-I in Alzheimer's disease", Trends Neurosci., 2003, 26(8): p. 404-6; J. Ren et al., "Insulin-like growth factor I as a cardiac hormone: physiological and pathophysiological implications in heart disease", J. Mol. Cell. Cardiol., 1999, 31(11): p. 2049-61). Because hIGF-I has cell proliferation activity, it can be also used in the production of antibody drugs and other biotechnology-based drugs as a medium additive for cells producing the proteins that are the active components of these drugs. Since production of biotechnology-based drugs is rising rapidly, demand for large quantities of hIGF-I is anticipated.

Under these circumstances, various methods have been reported for producing and refining hIGF-I by culturing transformed microorganisms by recombinant DNA methods (hereinafter referred to as recombinant microorganisms). For example, recombinant *E. coli* is used in U.S. Pat. No. 6,331,414, and recombinant yeast is used in U.S. Pat. No. 5,324,639.

In these methods, the recombinant *E. coli* or recombinant yeast is cultured to produce hIGF-I and the resulting hIGF-I is purified. Pigments, proteins and the like that are intrinsically produced by the *E. coli* or yeast also occur along with the target hIGF-I in the hIGF-I culture process and/or purification process, as does isomers having a different primary structure from hIGF-I.

One of the isomers, which is called misfolded hIGF-I because the combination of three pairs of disulfide bonds formed within the molecule differs from that of natural hIGF-I, is known to differ from natural hIGF-I not only in its physical properties but also in its biological properties (A. Sato et al., "Three-dimensional solution structure of a disulfide bond isomer of the human insulin-like growth factor-I", J. Pept. Res., 2000, 56(4), p. 218-30). Consequently, this isomer must be isolated and removed from the natural hIGF-I. Methods that have been reported for doing this include a method of isomerizing the isomer into natural hIGF-I and a method of isolating and removing the isomer (see for example U.S. Pat. Nos. 7,071,313; 5,231,178).

For industrial purposes, there need to be methods of producing hIGF-I at low cost and in large volume.

The applicant of the application previously discovered that when a recombinant coryneform bacterium is used as the host for producing human epithelial cell growth factor, the amount of intrinsic proteins produced in the culture liquid of the recombinant coryneform bacterium is less than the amount of intrinsic proteins produced in the culture liquid of other recombinant microorganisms (JP 2002-291476 A).

SUMMARY OF THE INVENTION

Because proteins intrinsically produced by bacterial cells are considered impurities when producing hIGF-I by secretion, it is desirable that the amount of such proteins be as small as possible. Expecting that by using a recombinant coryneform bacterium it would be possible to obtain hIGF-I while minimizing the amount of proteins intrinsically produced by the coryneform bacteria, the inventor of the application cultured recombinant coryneform bacteria to produce hIGF-I, and tried to obtain hIGF-I from the culture liquid. As a result, it was confirmed that the amount of proteins intrinsically produced by the coryneform bacteria could be minimized. At that time, it has been found modified hIGF-I (abbreviated as mhIGF-I) having a different molecular weight from hIGF-I was present in the culture liquid of recombinant coryneform bacteria. It is unknown whether mhIGF-I exists in nature. The inventor has also found that it has different physical properties from hIGF-I.

It is therefore an object of the invention to provide a method for producing hIGF-I with high purity and yield.

After exhaustive research aimed at achieving this object, the inventor discovered the surprising fact that when the pH of the culture liquid is made alkaline and the liquid is left standing after completion of culture, the amount of mhIGF-I decreases while hIGF-I increases. That is, the first embodiment of the present invention provides a method for manufacturing human insulin-like growth factor I, having a step of removing modified human insulin-like growth factor I from the human insulin-like growth factor I, the step including:

(A) a step of adjusting the pH of a culture liquid of a human insulin-like growth factor I producing bacteria to 8 or more after completion of culture;

(B) a step of letting the culture liquid obtained in step (A) stand; and (C) a step of removing the cell bodies from the culture liquid obtained in step (B).

The inventors also discovered that the amount of mhIGF-I decreases while the amount of hIGF-I increases if the cell bodies are removed from the culture liquid after completion of culture and the pH of the resulting culture liquid is made weakly acidic or alkaline and left standing. Consequently, the second embodiment of the invention provides a method for producing human insulin-like growth factor I, having a step of removing modified human insulin-like growth factor I from a culture liquid containing the human insulin-like growth factor I, the step including:

(a) a step of removing cell bodies from a culture liquid of a human insulin-like growth factor I producing bacteria;

(b) a step of adjusting the pH of the culture liquid obtained in step (a) to 5 or more; and (c) a step of letting the culture liquid obtained in step (b) stand.

The present invention also provides a method for manufacturing human insulin-like growth factor I, having (A) a step of adjusting the pH of a culture liquid of a human insulin-like growth factor I producing coryneform bacteria to 8 or more after completion of culture;

(B) a step of letting the culture liquid obtained in step (A) stand; and (C) a step of removing the cell bodies from the culture liquid obtained in (B), wherein no organic solvent is present in steps (A) and (B).

hIGF-I can be produced with high yield and purity by the present invention. Because complex purification steps for isolating and removing mhIGF-I are not used when manufacturing hIGF-I by the method of the present invention, high-purity hIGF-I can be produced easily at low cost. According to the method of the present invention, an amount of mhIGF-I equivalent to that removed by chromatography purification operations can be removed without any chromatography purification operations aimed at mhIGF-I removal when the culture liquid treatment conditions after completion of culture are selected appropriately.

BRIEF DESCRIPTION OF THE DRAWINGS

FIG. 1 shows the chromatogram of reverse-phase HPLC in Examples 1 and 2; "a" indicating the chromatogram of a culture liquid with cells removed prepared from a culture liquid after completion of culture but before addition of ethanol, "b" indicating the chromatogram of a culture liquid with cells removed prepared from a culture liquid that was left standing after completion of culture without ethanol addition or pH adjustment, and "c", "d", "e", "f" and "g" indicating the chromatograms of culture liquids with cells removed prepared from culture liquids left standing after ethanol addition and pH adjustment to about 9.0, 8.0, 6.8, 6.1 and 5.2, respectively; and "h" indicating the chromatogram of reverse-phase HPLC in Example 2, specifically indicating the chromatogram obtained by letting a culture liquid with cells removed prepared from a culture liquid after completion of culture stand and thereafter subjecting the culture liquid to reverse-phase HPLC.

DESCRIPTION OF THE PREFERRED EMBODIMENTS

Examples of the host bacteria of the human insulin-like growth factor I producing organism used in the present invention include the coryneform bacteria given in JP 2002-291476 A, including *Corynebacterium glutamicum* (abbreviated as *C. glutamicum*) ATCC13869 and the like.

A recombinant coryneform bacteria which has been modified to produce the human insulin-like growth factor I is preferably used as the human insulin-like growth factor I producing bacteria in the present invention, and the recombinant coryneform bacteria is preferably recombinant *Corynebacterium glutamicum*.

These bacteria can be cultured by usual methods under ordinary conditions. For example, they can be cultured in ordinary medium containing a carbon source, a nitrogen source and inorganic ions. Vitamins, amino acids and other organic micronutrients may also be added as necessary in order to enhance proliferation. Examples of carbon sources that can be used include glucose, sucrose and other carbohydrates, acetic acid and other organic acids, alcohols and the like. Nitrogen sources that can be used include ammonia gas, ammonia water, ammonium salts and the like. Inorganic ions as calcium ions, magnesium ions, phosphoric acid ions, potassium ions, iron ions and the like can be used appropriately as necessary. Culture is performed for about 1 to 7 days under aerobic conditions at a suitable pH range of 5.0 to 8.5 and temperature range of 15° C. to 37° C. Under these culture conditions, the target protein (hIGF-I) is produced in large quantity inside the bacterial cells and secreted efficiently outside the cells. In addition to the target hIGF-I, the culture liquid contains the by-product mhIGF-I, which has a different molecular weight from hIGF-I.

mhIGF-I is eluted more slowly than hIGF-I in reverse phase high-performance liquid chromatography (YMC-Pack C80C30S05-1046 WT column, particle size 5 μm, pore size 30 nm, bore 4.6 mm, height 100 mm (YMC Co.), flow rate 1 mL/min; eluted with eluent A: 0.1% TFA aq., eluent B: an aqueous solution of 0.1% TFA and 80% acetonitrile with a linear concentration gradient of 32 to 34%, based on the total amount of eluent A and eluent B (hereinafter same as above), of eluent B from 0 to 5 minutes, a linear concentration gradient of 34 to 39% eluent B from 5 to 16 minutes and a linear concentration gradient of 39 to 100% eluent B from 16 to 17 minutes, then washed as necessary). The molecular weight of mhIGF-I is 70 greater than that of hIGF-I, and the N-terminal of the mhIGF-I is blocked. The difference between a peptide consisting of amino acid residues 1 through 11 on the amino acid sequence of hIGF-I and a peptide consisting of amino acid residues 1 through 11 on the amino acid sequence of mhIGF-I in terms of the exact mass based on monoisotopic ions is 70.04. Collision-induced dissociation fragment ions are detected by tandem mass spectrometry of the peptide consisting of amino acid residues 1 through 11 on the amino acid sequence of mhIGF-I, by which an amino group of glycine residue in the N-terminus of mhIGF-I is estimated to be modified.

The first embodiment of the present invention is described below.

In step (A) of the present invention, the pH of the culture liquid is adjusted to 8 or more, preferably 9 or more, more preferably 9 to 10 after completion of culture or in other words after stopping aeration to the culture liquid. Ammonia gas, ammonia water (e.g., 28 mass %), sodium hydroxide aqueous solution (e.g., 1 mol/L) or the like can be used to adjust the pH.

In step (B) of the present invention, the culture liquid, which has been adjusted to a pH of 8 or more, is left standing. While the culture liquid is standing, its temperature is preferably −10° C. to 50° C., more preferably 10° C. to 40° C., yet more preferably 20° C. to 25° C. The standing time is preferably at least 2 hours, more preferably at least 4 hours, yet more preferably at least 12 hours. Even if the time is shorter, the amount of mhIGF-I will decrease and the amount of hIGF-I will increase, but the longer the standing time, the more hIGF-I can be collected. Because the bacterial cells continue to be active even after completion of culture, the pH of the culture liquid varies over time due to consumption of dissolved materials in the culture liquid or accumulation of metabolic products. Therefore, pH adjustment is preferably continued during the standing step so as to maintain the pH of the culture liquid at 8 or more, preferably 9 or more.

The culture liquid of the hIGF-I producing bacteria originally contains hIGF-I. According to the invention, the amount of mhIGF-I contained in the culture liquid after standing is reduced below that before standing by adjusting a pH of the culture liquid to 8 or more and then leaving the culture liquid to stand. Conversely, the amount of hIGF-I contained in the culture liquid after standing is increased above that before standing. The amount of increase in hIGF-I is sometimes greater than the amount of decrease in mhIGF-I. Although this is not definitely explained by any theory, it may be due to movement of hIGF-I present in the cell bodies and/or on the cell surfaces into the culture liquid, or due to isomerization of the hIGF-I isomer (misfolded hIGF-I) into hIGF-I during standing.

Purity measurement by reverse-phase high-performance liquid chromatography (hereinafter abbreviated as reverse-phase HPLC) has shown for example that the mhIGF-I content is about 20% of the amount of hIGF-I upon completion of culture, but that this is reduced to less than 1% after 16 hours of standing at 25° C.

Therefore, according to the method of the present invention, an amount of mhIGF-1 equivalent to that removed by chromatography purification operations designed to remove mhIGF-I can be removed without such operations by appropriately selecting the treatment conditions for the culture liquid after completion of culture, thereby greatly simplifying the purification operation.

In step (C) of the present invention, the hIGF-I producing bacteria are removed from the standing culture liquid. Examples of removal means include filtration, centrifugation and the like.

Following step (C) of the present invention, the hIGF-I solution obtained in step (C) can be further purified to remove impurities other than mhIGF-I too. High-purity hIGF-I can be isolated and purified by such means as salting out, ethanol precipitation, ultrafiltration, gel filtration chromatography, cation-exchange chromatography, anion-exchange chromatography, affinity chromatography, reverse-phase chromatography, hydrophobic chromatography and other suitable known means and combinations of such means.

An organic solvent may also be added in additional step (D) to the culture liquid before step (A), between step (A) and step (B) or during step (A). It can be added two or more times for example, such as before step (A) and during step (A).

As discussed above, the pH of the culture liquid normally varies after completion of culture. On an experimental scale, the cell bodies can be removed rapidly (in a few minutes for example) by e.g., centrifugation, thereby minimizing pH change due to cell activity. On an industrial scale, however, the cell removal operation takes more time (several hours for example), and the pH of the culture liquid may vary during this period. In the present invention, addition of an organic solvent serves to maintain the pH of the culture liquid, which has already been adjusted to pH 8 or more, at the adjusted pH while the culture liquid is standing. Ethanol or the like can be used as the organic solvent. The organic solvent is preferably selected from the group consisting of methanol, ethanol, propanol and acetonitrile. This facilitates pH control in step in which the organic solvent is added and its subsequent steps, and as necessary during the purification step that may be included after the method of the present invention.

The added amount of the organic solvent is preferably at least ¼ or more, more preferably ¼ to ⅓ of the total volume of the culture liquid.

The second embodiment of the present invention is explained here.

In step (a) of the present invention, the hIGF-I producing bacteria are removed from the culture liquid. Removal can be conducted by filtration, centrifugation or the like. The pH change of the culture liquid due to bacterial cell activity can be prevented by removing the hIGF-I producing cells from the culture liquid after completion of culture, preferably immediately after completion of culture. This facilitates pH control in step (a) and its subsequent steps, and as necessary during the purification step that may be included after the method of the present invention.

In step (b) of the present invention, the pH of the culture liquid after removal of the bacterial cells is adjusted to 5 or more. Immediately after completion of culture the pH is at the value set before the start of or during culture, but after cell removal the pH of the culture liquid varies depending on the time taken to remove the cells. When the pH of the culture liquid is less than 5 after cell removal, it is adjusted to 5 or more, preferably 6 or more, more preferably 6 to 10 using the ammonia gas or ammonia water (28 mass % for example) or sodium hydroxide aqueous solution (1 mol/L for example) described in the first embodiment.

In step (c) of the present invention, the culture liquid, which has been adjusted to a pH of 5 or more, is left standing. In this standing step, the amount of mhIGF-I contained in the culture liquid decreases while the amount of hIGF-I increases. The standing time and standing temperature are the same as in the first embodiment. The standing time is preferably at least 2 hours, more preferably at least 4 hours, yet more preferably at least 12 hours. Even in a shorter amount of time the amount of mhIGF-I will decrease and the amount of hIGF-I will increase, but more hIGF-I can be collected if the standing time is longer.

The culture liquid of the hIGF-I producing bacteria originally contains hIGF-I. According to the invention, the amount of mhIGF-I contained in the culture liquid after standing is reduced below that before standing by adjusting a pH of the culture liquid from which hIGF-I producing strain has been removed to 5 or more and then leaving the culture liquid to stand. Conversely, the amount of hIGF-I contained in the culture liquid after standing is increased above that before standing. The amount of increase in hIGF-I is sometimes greater than the amount of decrease in mhIGF-I. Although this is not definitely explained by any theory, it may be due to isomerization of the hIGF-I isomer (misfolded hIGF-I) in the culture liquid into hIGF-I during standing.

Purity measurement by reverse-phase HPLC has shown for example that the mhIGF-I content is about 20% of the amount of hIGF-I upon completion of culture, but that this is reduced to less than 1% after 20 hours of standing at 25° C.

Therefore, according to the method of the present invention an amount of mhIGF-1 equivalent to that removed by chromatography purification operations designed to remove mhIGF-I can be removed without such operations by appropriately selecting the treatment conditions for the culture liquid after completion of culture, thereby greatly simplifying the purification operation.

After step (c) of the present invention, the hIGF-I solution obtained in step (c) can be further purified to remove impurities other than mhIGF-I too. The purification means are as described in the first embodiment.

An organic solvent can be added in additional step (d) to the culture liquid before step (a) or during step (a). Addition of an organic solvent serves to maintain the pH of the culture liquid at the beginning of step (a) or during step (a). Ethanol or the like can be used as the organic solvent. The organic solvent is preferably selected from the group consisting of methanol, ethanol, propanol and acetonitrile. By adding an organic solvent, it is possible to prevent change in the pH of the culture liquid due to the activity of the bacteria. This facilitates pH control in step in which the organic solvent is added and its subsequent steps, and as necessary during the purification step that may be included after the method of the present invention.

The added amount of the organic solvent is preferably at least ¼, more preferably ¼ to ⅓ of the total volume of the culture liquid.

When analyzing hIGF-I and mhIGF-I, the following items can all be performed by ordinary means that are common practice in the field:
- content determination, purity determination and fractioning by reverse-phase HPLC;
- N-terminal sequencing by N-terminal sequencer;
- molecular mass determination by various mass spectrometer;
- to obtain structural information by tandem mass spectrometry;
- biological activity measurement based on cell proliferation activity; and
- limited degradation by protease, carboxymethylation of cysteine.

EXAMPLES

Examples and comparative examples of the present invention are explained in more detail below, but the present invention is not limited by these examples.

Reference Example

Secretion of hIGF-I Using Fused Gene Having the Signal Sequence of Corynebacterium ammoniagenes ATCC6872 Cell Surface Protein and Sequence Coding for hIGF-I
(1) "Construction of hIGF-I Gene"

Since the amino acid sequence of hIGF-I has already been determined (J. Biol. Chem., 1978, 253(8): p. 2769-76), a nucleotide sequence was constructed so as to code for this amino acid sequence. The primers represented by SEQ ID NOS:1 through 6 were synthesized with reference to the constructed nucleotide sequence. Then using the primers represented by SEQ ID NOS:1 through 6 as a template, a PCR reaction was performed with the primers represented by SEQ ID NOS:1 through 6. Next, using the resulting PCR reaction product DNA as the template, PCR was then performed again with the primers represented by SEQ ID NOS:7 and 8. The primer represented by SEQ ID NO:8 includes the recognition sequence of the restriction enzyme XbaI, which is necessary for insertion into a plasmid.

In agarose gel electrophoresis, a roughly 0.2 kb amplified fragment was detected from the PCR reaction. This fragment was collected from the agarose gel using Easy Trap Ver. 2 (Takara Co.). The collected DNA was purified with a DNA Clean-UP system (Promega), and inserted into the SmaI site of the pVC7 described in JP 09-070291 A to obtain pVCIGFm. The nucleotide sequence of the inserted fragment was determined using a dye terminator cycle sequencing kit (PE Applied Biosystems) and a 377A DNA sequencer (PE Applied Biosystems), thereby confirming that the expected gene had been constructed.

SEQ ID NO: 1
5'-GGCCCTGAAACTCTGTGTGGTGCCGAACTGGTGGATGCCTTGCAGTTTGT-3'

SEQ ID NO: 2
5'-TTGTTAAAATAGAAGCCGCGATCGCCGCACACAAACTGCAAGGCATCCAC-3'

SEQ ID NO: 3
5'-CGCGGCTTCTATTTTAACAAACCAACCGGTTACGGTTCCAGCTCCCGCCG-3'

SEQ ID NO: 4
5'-CACTCATCGACGATTCCGGTTTGTGGAGCGCGGCGGGAGCTGGAACCGTA-3'

SEQ ID NO: 5
5'-ACCGGAATCGTCGATGAGTGCTGTTTCCGCAGCTGCGACCTCCGCCGCCT-3'

SEQ ID NO: 6
5'-GCCTCTAGATCATGCGGATTTTGCGGGCTTCAGGGGTGCGCAGTACATCTCCAGGCGGCGGAGGTCGCAGCT-3'

SEQ ID NO: 7
5'-GGCCCTGAAACTCTGTGTGG-3'

SEQ ID NO: 8
5'-GCCTCTAGATCATGCGGATTTTGCGGGCT-3'

(2) "Construction of hIGF-I Gene Having the Promoter Sequence of C. glutamicum ATCC13869 Cell Surface Protein (cspB) and the Signal Sequence of Corynebacterium ammoniagenes ATCC6872 Cell Surface Protein"

A pro-transglutaminase fused gene having the promoter sequence of C. glutamicum ATCC13869 cell surface protein gene (cspB) and the signal sequence of Corynebacterium ammoniagenes (abbreviated as C. Ammoniagenes) ATCC6872 cell surface protein has already been constructed and cloned on a plasmid as pPSPTG1 (Y. KIKUCHI et al., "Secretion of active-form Streptoverticillium mobaraense transglutaminase by Corynebacterium glutamicum: processing of the pro-transglutaminase by a cosecreted subtilisin-like protease from Streptomyces albogriseolus", Appl. Environ. Microbiol., 2003, 69(1): p. 358-66).

The primers represented by SEQ ID NOS:9 and 10 were synthesized with reference to the gene sequence of the C. glutamicum ATCC13869 cell surface protein (cspB), and PCR was performed with pPSPTG1 as the template. The primer represented by SEQ ID NO:10 includes a sequence coding for the N-terminal amino acid of hIGF-I for purposes of constructing a fused gene with the hIGF-I gene.

SEQ ID NO: 9
5'-GGCGGTACCCAAATTCCTGTGAATTAGCTG-3'

SEQ ID NO: 10
5'-CCACACAGAGTTTCAGGGCCTGCCGTTGCCACAGGTGCGG-3'

The primers of SEQ ID NOS:7 and 8 of Reference Example (1) were also used to amplify a region coding for hIGF-I by PCR from the plasmid pVCIGF constructed in Reference Example (1), which includes the sequence of the hIGF-I gene.

Next, 1 µl of PCR reaction solution including the amplified gene coding for the promoter of C. glutamicum ATCC13869 cell surface protein (cspB) and the signal sequence of C. ammoniagenes ATCC6872 cell surface protein was mixed with 1 µL of PCR reaction solution including the amplified hIGF-I gene region and used as the template for crossover PCR using SEQ ID NOS:9 and 8, to thereby amplify a fused gene comprising hIGF-I linked to a region coding for the promoter gene of C. glutamicum ATCC13869 cell surface protein (cspB) and the signal sequence of C. ammoniagenes ATCC6872 cell surface protein. A roughly 0.9 kb amplified fragment was detected in agarose gel electrophoresis. This fragment was collected from the agarose gel using Easy Trap Ver. 2 (Takara Co.). The collected DNA was cleaved with the restriction enzymes KpnI and XbaI (Takara Co.), purified with a DNA Clean-UP system (Promega), and inserted into the a KpnI-XbaI site of the pPK4 plasmid (including kanamycin-resistant gene) described in JP 09-322774 A to obtain pPSIGFm. The nucleotide sequence of the inserted fragment was determined using a dye terminator cycle sequencing kit (PE Applied Biosystems) and a 377A DNA sequencer (PE Applied Biosystems), thereby confirming that the expected fused gene had been constructed.

(3) "Preparation of hIGF-I Producing Strain"

*C. glutamicum* AJ12036 (FERM BP-734) (WO/2002/081694, description) was transformed by electroporation with the hIGF-I expressing plasmid pPSIGFm prepared in (2) to obtain a kanamycin-resistant strain.

Example 1

(1) "Preparation of Recombinant Coryneform Bacterium Culture Liquid"

After being grown overnight at 30° C. in CM2G agar medium (yeast extract 10 g, tryptone 10 g, glucose 5 g, NaCl 5 g, agar 15 g, water up to 1 L) containing 25 mg/L kanamycin, the hIGF-I producing strain prepared in (3) was seeded in a 500 mL Sakaguchi flask containing 20 mL of CM2G liquid medium (yeast extract 10 g, tryptone, 10 g, glucose 5 g, NaCl 5 g, water up to 1 L) containing 25 mg/L kanamycin, cultured overnight at 30° C. and used as the seed culture. For the main culture, a 1 liter jar fermenter was filled with 300 mL of MMTG liquid medium (glucose 120 g, $CaCl_2$ 2 g, $MgSO_4$-$7H_2O$ 3 g, $MnSO_4$-$4H_2O$ 0.03 g, $FeSO_4$-$7H_2O$ 0.03 g $(NH_4)_2SO_4$ 3 g, $KH_2PO_4$ 1.5 g, thiamine hydrochloride 450 µg, biotin 450 µg, DL-methionine 0.15 g, pH 6.7, water to 1 L), seeded with 5% (15 mL) using the seed culture, and then shaking cultured with aeration for 3 days at 30° C. with the pH maintained at 6.7 by addition of ammonia gas.

(2) "pH Adjustment and Standing of Culture Liquid After Completion of Culture"

After completion of culture, the culture liquid was cooled to 25° C. and maintained at that temperature, and then gently shaken continuously as ethanol was added in the amount of ¼ the volume of culture liquid. After addition of ethanol the pH of the culture liquid was 6.8. The pH was measured at 25° C. using a calibrated glass electrode (as in all cases below). Immediately after completion of ethanol addition, the culture liquid was separated into multiple parts, and the pH of each was adjusted to about 9.0, about 8.0, about 6.8, about 6.1 and about 5.2 with 10 mass % acetic acid or 10 mass % ammonia water. The pH of about 6.8, about 6.1 and about 5.2 was used as a comparative example. After pH adjustment, the culture liquid was left standing for about 17 hours at 25° C. with gentle agitation. As a negative control, part of the culture liquid after completion of culture was left standing for about 17 hours at 25° C. with gentle agitation.

Even after about 17 hours of standing, the pH values of the culture liquids that were pH adjusted after ethanol addition remained at the adjusted values. On the other hand, the pH of the negative control was found to vary, and was about 5.6 after about 17 hours of standing.

(3) "Removal of Cell Bodies from Culture Liquid"

Each culture liquid was transferred to a microtube, and the cell bodies were isolated by 10 minutes of centrifugation at 15,000 rpm using a small centrifuge. The resulting supernatant was filtered with a fine 0.2 µm sterilizing filter, and the resulting filtrate was used as the culture liquid with cells removed.

(4) "Evaluation of hIGF-I Purity and Yield"

The purity and yield of hIGF-I in the culture liquid with cells removed was evaluated by reverse-phase HPLC. The results are shown as "a" through "g" in FIG. 1. In FIG. 1, "a" indicates the chromatogram of a culture liquid with cells removed prepared from a culture liquid after completion of culture but before addition of ethanol, "b" indicates the chromatogram of a culture liquid with cells removed prepared from a culture liquid that was left standing after completion of culture without ethanol addition and pH adjustment, and "c", "d", "e", "f" and "g" indicate the chromatograms of culture liquids with cells removed prepared from culture liquids left standing after ethanol addition and pH adjustment to about 9.0, about 8.0, about 6.8, about 6.1 and about 5.2, respectively. In FIG. 1, the peak appearing near a retention time of 11.7 minutes is the hIGF-I peak. The small peak appearing to the lower right of the hIGF-I peak near a retention time of 12.2 minutes is the mhIGF-I peak. From "a", it is clear that mhIGF-I occurs as a by-product upon completion of culture. From "b" it can be seen that hIGF-I declines and mhIGF-I increases in culture liquid without pH adjustment. Comparing "c", "d", e "f" and "g", it can be seen that the amount of mhIGF-I varies according to pH, and decreases at pH 8 and above. Comparing the chromatograms from "a" to "g", it can be seen that the highest hIGF-I peak height and the lowest mhIGF-I peak height are achieved when the culture liquid is adjusted to a pH of 9 and left standing. Given 100% as the amount of hIGF-I determined from the "a" chromatogram (hIGF-I immediately after completion of culture), the amount of mhIGF-I determined from the "a" chromatogram (mhIGF-I immediately after completion of culture), the amount of hIGF-I determined from the "c" chromatogram (hIGF-I after standing) and the amount of mhIGF-I determined from the "c chromatograph (mhIGF-I after standing) are 20%, 140% and 0%, respectively.

The column used for reverse-phase HPLC was a YMC-Pack C8 OC30S05-1046WT with a particle diameter of 5 µm, a pore size of 30 nm, an inner diameter of 4.6 mm and a height of 100 mm (YMC Co.), at a flow rate of 1 mL/min. Elution was accomplished with eluent A: 0.1% TFA aq., eluent B: an aqueous solution of 0.1% TFA and 80% acetonitrile with a linear concentration gradient of 32 to 34% eluent B from 0 to 5 minutes, a linear concentration gradient of 34 to 39% eluent B from 5 to 16 minutes and a linear concentration gradient of 39 to 100% eluent B from 16 to 17 minutes, followed by washing as necessary. The same applies to Example 2.

Test Examples

"Confirming Structure and Properties of hIGF-I and mhIGF-I"

A culture liquid with cells removed obtained in the same way as the culture liquid with cells removed of "a" in FIG. 1 was subjected to reverse-phase HPLC, and the peak appearing near a retention time of 11.7 minutes and the peak appearing to the lower right of this peak near a retention time of 12.2 minutes were each fractioned. This fractioning process was repeated multiple times to obtain hIGF-I and mhIGF-I samples of sufficient quantity for the following analysis. The resulting samples were then each concentrated to dryness, and the hIGF-I sample was subjected to mass spectrometry, N-terminal amino acid sequencing and biological activity measurement, while the mhIGF-I sample was subjected to mass spectrometry and N-terminal amino acid sequencing. As a result, the hIGF-I sample yielded analytical results from mass spectrometry, N-terminal amino acid sequencing and biological activity measurement that were comparable to those of commercial hIGF-I (Peprotech, Inc. Human IGF-I Cat. #100-11), which was measured for purposes of comparison. The mhIGF-I was shown by mass spectrometry to have a molecular weight just 70 greater than that of hIGF-I, and by N-terminus amino acid sequencing to have a blocked N-terminal. Mass spectrometry was performed using a Bruker Daltonics MicrOTOF electrospray time-of-flight mass spectrometer, and N-terminal amino acid sequencing using a Shimadzu PPSQ-21A automated protein sequencer. The biological activity was determined based on cell proliferation activity using MCF-7 cells (ATCC #HTB-22) by reference to Cancer Research, 1988. 48: p. 4083-92.

Next, the concentrated and dried mhIGF-I sample was subjected to limited degradation with the protease Asp-N (Roche Diagnostics GmbH, Endoproteinase Asp-N, Cat. No. 11420488001) and then to carboxymethylation of cysteine, and the resulting peptide mixture was analyzed by capillary liquid chromatography/tandem mass spectrometry. As a result, ions were detected from a peptide having a molecular weight just 70 greater than the molecular weight of a peptide consisting of amino acid residues 1 through 11 on the amino acid sequence of hIGF-I. Moreover, analysis of collision-induced dissociation fragment ions derived from these parent ions revealed ions from a peptide having a molecular weight just 70 greater than the molecular weight of a peptide consisting of amino acid residues 1 through 3 on the amino acid sequence of hIGF-I. This shows that mhIGF-I is N-terminal modified hIGF-I, and is a molecular species having a molecular weight just 70 greater than that of hIGF-I. Capillary liquid chromatography/tandem mass spectrometry was performed using a ThermoScientific Co. LCQ ion-trap mass spectrometer.

Further, the hIGF-I sample and mhIGF-I sample concentrated and dried in the same manner as described above were subjected to limited degradation with Asp-N and then to carboxymethylation of cysteine, and the resulting peptide mixture of each sample was analyzed by reverse-phase HPLC. Then, a peptide consisting of amino acid residues 1 through 11 from hIGF-I and a peptide consisting of amino acid residues 1 through 11 from mhIGF-I were fractioned. After concentrated and dried, each peptide was dissolved into 50% methanol aqueous solution containing 2% acetic acid to form a solution of N-terminal peptide from hIGF-I and a solution of N-terminal peptide from mhIGF-I. The resulting solutions were blended together and then subjected to high-resolution mass spectrometry. As a result, it was confirmed that two molecular species having about 1147 and about 1217 of m/z of monoisotopic ions were included in the solutions. The exact mass difference therebetween was 70.04. The column used for reverse-phase HPLC was a SunFire (trade mark) C18 with a particle diameter of 5 μm, an inner diameter of 4.6 mm and a height of 150 mm (Nihon Waters K.K.), at a flow rate of 1 mL/min. Elution was accomplished with eluent A: 0.1% TFA a.q., eluent B: an aqueous solution of 0.1% TFA and 80% acetonitrile with a linear concentration gradient of 0% eluent B from 0 to 5 minutes, a linear concentration gradient of 0 to 15% eluent B from 5 to 6 minutes, and a linear concentration gradient of 15 to 45% eluent B from 6 to 36 minutes, followed by washing as necessary. The peak of the peptide consisting of amino acid residues 1 through 11 of hIGF-I appeared near a retention time of 25 minutes. The peak of the peptide consisting of amino acid residues 1 through 11 of mhIGF-I appeared near a retention time of 26 minutes. Mass spectrometry was performed using a Bruker Daltonics Fourier Transform ion cyclotron mass spectrometer APEX-II 70e.

In addition, the solution of N-terminal peptide from hIGF-I and the solution of N-terminal peptide from mhIGF-I obtained above were subjected to matrix-assisted laser desorption/ionization tandem time-of-flight mass spectrometer, respectively, to compare collision-induced dissociation fragment ions derived from the parent ions of the peptide having about 1147 of m/z of monoisotopic ions and those of the peptide having about 1217 of m/z of monoisotopic ions. Then it was revealed that only the peptide having about 1217 of m/z of monoisotopic ions produced ions having m/z of about 100. The resulting ions having m/z of about 100 was considered to be a1 ions produced from the peptide consisting of amino acid residues 1 through 11 of mhIGF-I by collision-induced dissociation. This is because the mass of the a1 ions from N-terminal glycine produced from the peptide consisting of amino acid residues 1 through 11 of hIGF-I by collision-induced dissociation is 30, to which 70 is added makes 100. It was estimated that the peptide consisting of amino acid residues 1 through 11 of mhIGF-I had a molecular weight 70 greater than that of hIGF-I at the amino group of N-terminal glycine. Matrix-assisted laser desorption/ionization tandem time-of-flight mass spectrometry was performed using a Shimadzu AXIMA-TOF2 in which α-cyano-4-hydroxycinnamic acid was used as matrix.

Example 2

"Changes in Amount of mIGF-I During Standing Following Removal of hIGF-I Producing Bacteria After Completion of Culture"

The culture liquid with cells removed indicated by "a" in FIG. 1 was left standing for about 20 hours at 25° C. The pH of the culture liquid was 6.4 at the start of standing and did not change on completion of standing.

After completion of standing, the purity and yield of hIGF-I in this culture liquid with cells removed was evaluated by reverse-phase HPLC. The results are indicated by "h" in FIG. 1. Under these conditions, mhIGF-I declines while hIGF-I increased. Given 100% as the amount of hIGF-I determined from the "a" chromatograph, the amount of hIGF-I determined from the "h" chromatogram (hIGF-I after standing) and the amount of mhIGF-I determined from the "h" chromatogram" (mhIGF-I after standing) were 120% and 0%, respectively.

hIGF-I obtained by the method of the present invention can be used as a medium additive for cells, e.g., CHO cells, used to produce proteins as active ingredients for biotechnology-based drugs.

What is claimed is:

1. A method for producing human insulin-like growth factor I, comprising removing N-terminal blocked human insulin-like growth factor I from the human insulin-like growth factor I, wherein said removing comprises:
   (A) adjusting the pH of a culture liquid of a human insulin-like growth factor I producing recombinant coryneform bacteria to 8 or more after completion of culture;
   (B) letting the culture liquid obtained in (A) stand for 2 hours or more at −10° C. to 50° C.; and
   (C) removing the producing bacteria from the culture liquid obtained in (B).

2. The production method according to claim 1, wherein said recombinant coryneform bacteria is recombinant Corynebacterium glutamicum.

3. The production method according to claim 1, further comprising
   (D) adding an organic solvent to said culture liquid either before (A), after (A) and before (B), or during (A).

4. The production method according to claim 3, wherein said organic solvent is selected from the group consisting of methanol, ethanol, propanol and acetonitrile.

5. The production method according to claim 1, wherein said culture liquid is let stand for 4 hours or more in (B).

6. The production method according to claim 1, wherein said culture liquid is let stand at 10° C. to 40° C. in (B).

7. A method for producing human insulin-like growth factor I, comprising removing N-terminal blocked human insulin-like growth factor I from a culture liquid containing the human insulin-like growth factor I, wherein said removing comprises:
   (a) removing a human insulin-like growth factor I producing bacteria from a culture liquid of the producing bacteria, wherein said human insulin-like growth factor I producing bacteria is a recombinant coryneform bacteria;
   (b) adjusting the pH of the culture liquid obtained in (a) to 5 or more; and
   (c) letting the culture liquid obtained in (b) stand for 2 hours or more at −10° C. to 50° C.

8. The production method according to claim 7, wherein said recombinant coryneform bacteria is recombinant Corynebacterium glutamicum.

9. The production method according to claim 7, further comprising
   (d) adding an organic solvent to said culture liquid either before (a) or during (a).

10. The production method according to claim 9, wherein said organic solvent is selected from the group consisting of methanol, ethanol, propanol and acetonitrile.

11. The production method according to claim 7, wherein said culture liquid is let stand for 4 hours or more in (c).

12. The production method according to claim 7, wherein said culture liquid is let stand at 10° C. to 40° C. in (c).

13. A method for producing human insulin-like growth factor I, comprising:

(A) adjusting the pH of a culture liquid of a human insulin-like growth factor I producing recombinant coryneform bacteria to 8 or more after completion of culture;
(B) letting the culture liquid obtained in (A) stand for 2 hours or more at −10° C. to 50° C.; and
(C) removing the cell bodies from the culture liquid obtained in (B),
wherein no organic solvent is present in (A) and (B).

* * * * *